United States Patent
Linhardt et al.

(10) Patent No.: US 9,901,247 B2
(45) Date of Patent: Feb. 27, 2018

(54) METHODS FOR ADHERING A SUBSTRATE TO A POLYMER LAYER

(71) Applicant: Verily Life Sciences LLC, Mountain View, CA (US)

(72) Inventors: Jeffrey George Linhardt, Mountain View, CA (US); Zenghe Liu, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 644 days.

(21) Appl. No.: 13/930,687

(22) Filed: Jun. 28, 2013

(65) Prior Publication Data

US 2015/0005602 A1    Jan. 1, 2015

(51) Int. Cl.
  B29C 47/00    (2006.01)
  B29C 65/00    (2006.01)
  (Continued)

(52) U.S. Cl.
  CPC ........ *A61B 3/101* (2013.01); *B29D 11/00048* (2013.01); *B29D 11/00817* (2013.01); *B29C 65/522* (2013.01); *B32B 37/185* (2013.01); *B32B 2551/00* (2013.01); *G02C 7/04* (2013.01); *G02C 7/049* (2013.01); *G02C 2202/16* (2013.01)

(58) Field of Classification Search
  CPC ...... G02C 7/04; G02C 7/049; G02C 2202/16; B29D 11/00038; B29D 11/00048; A61B 5/14507; A61B 5/14532; A61B 5/6821; A61B 3/101; B32B 2551/00; B32B 37/12; B32B 37/18; B32B 37/182; B32B 37/185; B29C 65/48; B29C 65/52; B29C 65/522

USPC ............ 156/60, 61, 242, 245, 272.2, 275.5, 156/275.7, 290, 291, 292, 295, 307.1;
(Continued)

(56) References Cited

U.S. PATENT DOCUMENTS 2,664,025 A * 12/1953 Herman ................ B29C 43/021
                                                    264/1.7
3,916,033 A * 10/1975 Merrill ............. B29D 11/00076
                                                    156/272.2
(Continued)

FOREIGN PATENT DOCUMENTS

WO    2014113131 A1    7/2014

OTHER PUBLICATIONS

PCT International Search Report and Written Opinion, PCT Application No. PCT/US2014/033998, dated Sep. 5, 2014.
(Continued)

*Primary Examiner* — Philip Tucker
*Assistant Examiner* — Brian R Slawski
(74) *Attorney, Agent, or Firm* — McDonnell Boehnen Hulbert & Berghoff LLP

(57) ABSTRACT

The present disclosure provides a method including forming a polymer layer defining a side of an eye-mountable device. The method may also include providing an adhesive in a ring-shaped pattern on a ring-shaped substrate or on the first polymer layer. The method may also include providing the ring-shaped substrate on the first polymer layer in a predetermined rotational orientation. The method may also include applying a force to one or more of the ring-shaped substrate and the polymer layer to adhere the first polymer layer to the ring-shaped substrate. The method may also include curing the ring-shaped substrate and the first polymer layer.

13 Claims, 11 Drawing Sheets

(51) Int. Cl.
   *B32B 37/00* (2006.01)
   *B32B 38/10* (2006.01)
   *A61B 5/05* (2006.01)
   *G02C 7/00* (2006.01)
   *G02C 7/02* (2006.01)
   *G02C 7/04* (2006.01)
   *B29D 11/00* (2006.01)
   *A61B 3/10* (2006.01)
   *B29C 65/52* (2006.01)
   *B32B 37/18* (2006.01)

(58) Field of Classification Search
   USPC ......... 600/347; 623/4.1; 351/159.02, 159.33, 351/159.73, 178; 264/1.1, 1.7, 2.6
   See application file for complete search history.

(56) References Cited

U.S. PATENT DOCUMENTS

| | | | | |
|---|---|---|---|---|
| 4,619,793 A * | 10/1986 | Lee | ............... | B29D 11/00076 264/1.1 |
| 2003/0035083 A1 * | 2/2003 | Francis | ............ | B29D 11/00038 351/159.02 |
| 2004/0096666 A1 * | 5/2004 | Knox | ............... | B32B 27/08 428/412 |
| 2004/0207808 A1 | 10/2004 | Fleischman et al. | | |
| 2005/0275137 A1 * | 12/2005 | Stolpe | ............... | A61F 2/141 264/294 |
| 2007/0212518 A1 * | 9/2007 | Begon | ............... | B29C 41/32 428/128 |
| 2007/0291224 A1 | 12/2007 | Lai | | |
| 2008/0027304 A1 * | 1/2008 | Pardo | ............... | A61F 9/00781 600/399 |
| 2009/0048671 A1 * | 2/2009 | Lipshitz | ............... | A61F 2/1613 623/6.31 |
| 2009/0256977 A1 * | 10/2009 | Haddock | ............ | B29D 11/00028 349/13 |
| 2010/0053549 A1 * | 3/2010 | Legerton | ............ | B29D 11/00048 351/159.27 |
| 2010/0103368 A1 | 4/2010 | Amirparviz et al. | | |
| 2010/0178722 A1 | 7/2010 | de Graff et al. | | |
| 2011/0317277 A1 * | 12/2011 | Pugh | ............... | G02C 7/085 359/665 |
| 2012/0089113 A1 | 4/2012 | Ambati et al. | | |
| 2012/0236524 A1 | 9/2012 | Pugh et al. | | |
| 2012/0245444 A1 | 9/2012 | Otis et al. | | |
| 2012/0287395 A1 * | 11/2012 | Tamura | ............... | C03C 27/10 351/49 |
| 2012/0302861 A1 | 11/2012 | Marshall et al. | | |
| 2013/0041245 A1 | 2/2013 | Cerboni | | |
| 2013/0055819 A1 | 3/2013 | Yan | | |
| 2013/0135578 A1 | 5/2013 | Pugh et al. | | |
| 2013/0152386 A1 * | 6/2013 | Pandojirao-S | ............ | H05K 3/16 29/842 |
| 2014/0192313 A1 * | 7/2014 | Riall | ............... | G02C 7/04 351/158 |
| 2014/0268024 A1 * | 9/2014 | Pugh | ............... | G02C 7/048 351/159.24 |

OTHER PUBLICATIONS

Extended European Search Report, dated Dec. 12, 2016, in European Patent Application No. 14817275.2.

* cited by examiner

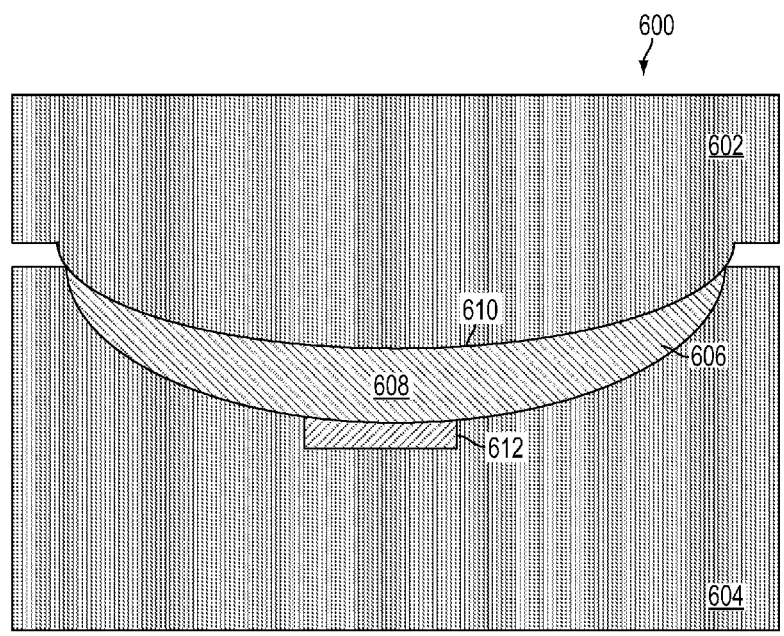
FIG. 6A
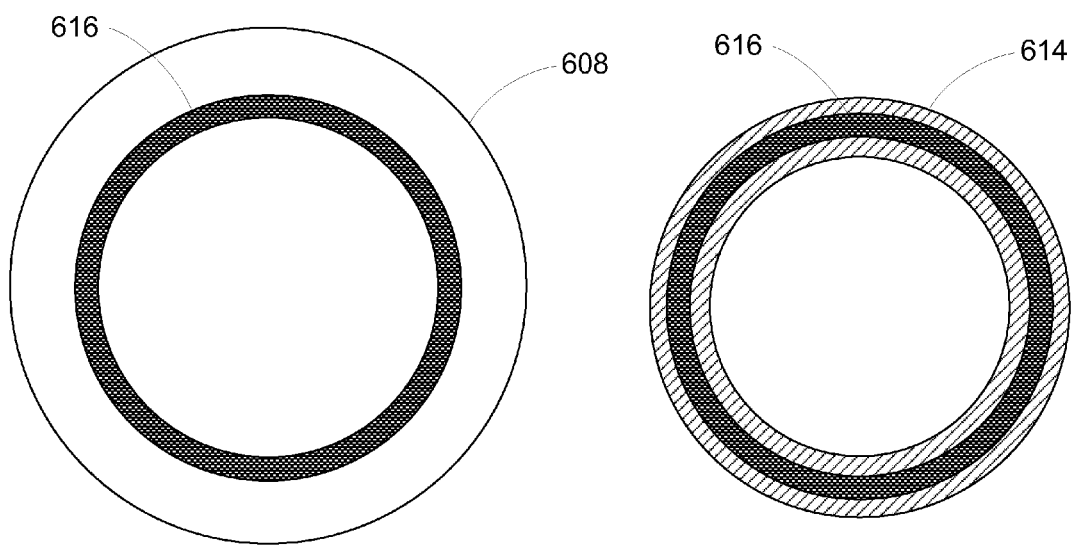
FIG. 6B  FIG. 6C

METHODS FOR ADHERING A SUBSTRATE TO A POLYMER LAYER

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose in a tear film of a user wearing the eye-mountable device). The body-mountable device may also be configured to monitor various other types of health-related information.

SUMMARY

In one embodiment, the present disclosure provides a method including forming a polymer layer defining a side of an eye-mountable device. The method may also include providing an adhesive in a ring-shaped pattern on a ring-shaped substrate or on the first polymer layer. The method may also include providing the ring-shaped substrate on the first polymer layer in a predetermined rotational orientation. The method may also include applying a force to one or more of the ring-shaped substrate and the polymer layer to adhere the first polymer layer to the ring-shaped substrate. The method may also include curing the ring-shaped substrate and the first polymer layer.

In another embodiment, the present disclosure provides another method including forming a first layer of a bio-compatible material. The method may also include providing an adhesive in a ring-shaped pattern on a ring-shaped substrate or on the first layer of the bio-compatible material. The method may also include providing the ring-shaped substrate on the first layer of the bio-compatible material in a predetermined rotational orientation. The method may also include applying a force to one or more of the ring-shaped substrate and the polymer layer to adhere the first layer of the bio-compatible material to the ring-shaped substrate. The method may also include forming a second layer of the bio-compatible material to cover the ring-shaped substrate. The method may also include annealing the first layer of the bio-compatible material and the second layer of the bio-compatible material together to form an encapsulated structure. The encapsulated structure includes the ring-shaped substrate fully enclosed between the first layer of the bio-compatible material and the second layer of the bio-compatible material.

In yet another embodiment, the present disclosure provides an eye-mountable device. The eye-mountable device may include a first polymer layer that defines a posterior side of the eye-mountable device, which may be configured to be removably mounted over a corneal surface. The eye-mountable device may also include a second polymer layer that defines an anterior side of the eye-mountable device, which may be configured to be compatible with eyelid motion. The eye-mountable device may also include a ring-shaped substrate at least partially embedded between the first polymer layer and the second polymer layer. The ring-shaped substrate may be coupled to the first polymer layer via an adhesive provided in a ring-shaped pattern on the ring-shaped substrate or on the first polymer layer. The ring-shaped structure may be coupled to the first polymer layer in a predetermined rotational orientation. The eye-mountable device may also include an electronics module on the ring-shaped substrate. The electronics module may include an electrochemical sensor having a working electrode and a reference electrode, an antenna, and a controller. The controller may be electronically connected to the electrochemical sensor and the antenna, and the controller may be configured to control the electrochemical sensor to obtain a sensor measurement related to a concentration of an analyte in a fluid to which the eye-mountable device is exposed and use the antenna to indicate the sensor measurement.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6A is an illustration of formation of a first polymer layer, according to an example embodiment.

FIG. 6B is an illustration of providing an adhesive in a ring-shaped pattern on a polymer layer.

FIG. 6C is an illustration of providing an adhesive in a ring-shaped pattern on a ring-shaped substrate.

DETAILED DESCRIPTION

Figure 1:
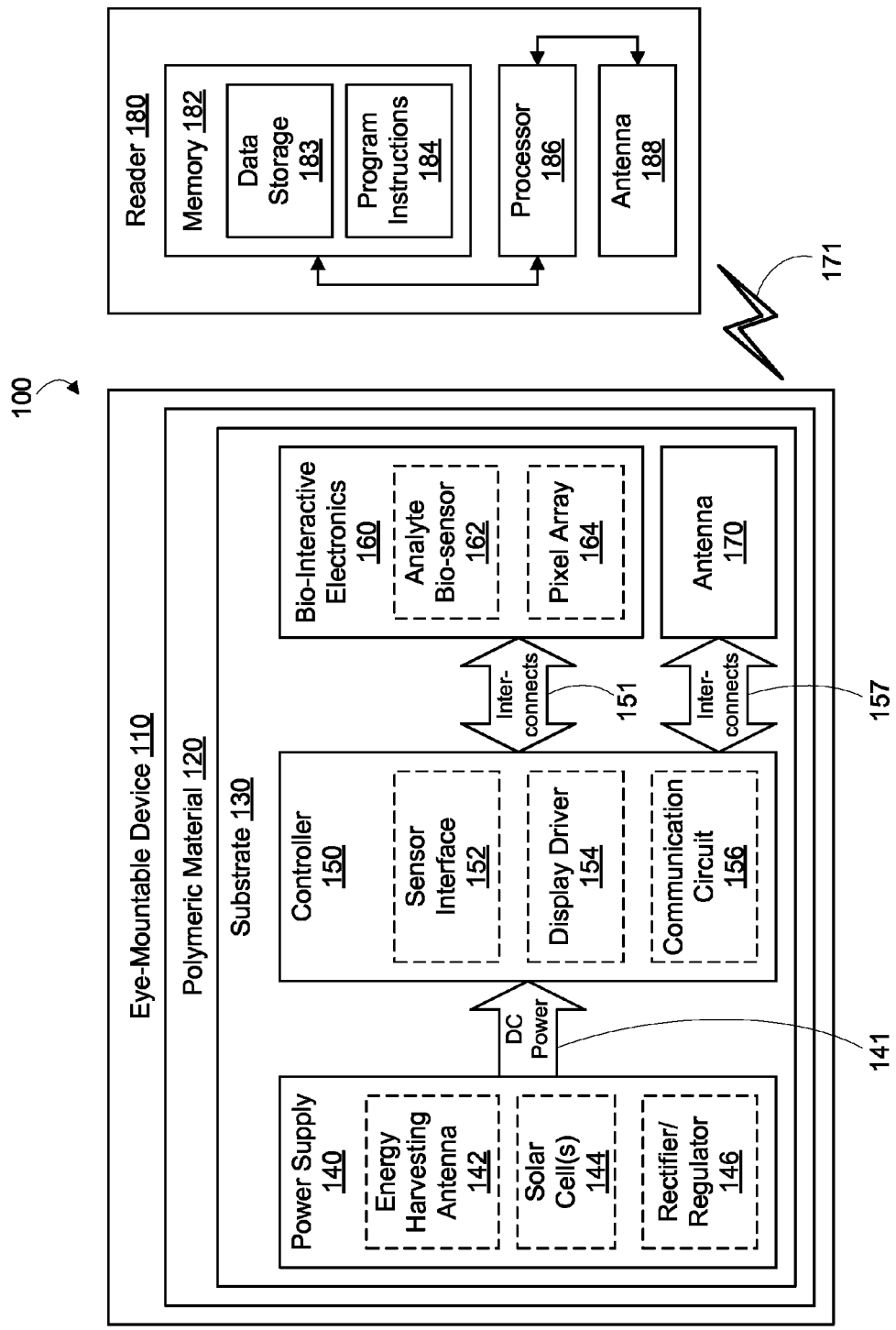
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A body-mountable device, such as a contact lens, may be configured to monitor health-related information based on at least one analyte detected in a fluid of a user wearing the body-mountable device. An example body-mountable device that comprises an eye-mountable device may include an embedded sensor configured to detect an analyte in a tear film of a user wearing the eye-mountable device, such as glucose. With such an arrangement, the analyte sensor may monitor health-related information, such as glucose level or corneal oxygen concentration. The example eye-mountable device will now be described in greater detail.

The exposed regions of the example eye-mountable device may include a polymeric material formed to be contact-mounted to a corneal surface of an eye of a user. The polymeric material may include a first polymer layer defining a first side of the eye-mountable device, and a second layer defining an anterior side of the eye-mountable device. A substrate may be embedded in the polymeric material to provide a mounting surface for a power supply, a controller, an analyte sensor, and a communication antenna, as examples. The substrate may be shaped as a flat, circular ring (e.g., a disk with a central hole). In one embodiment, the substrate may be shaped as a ring with a diameter of about 10 millimeters, a radial width of about 1 millimeter (e.g., an outer radius about 1 millimeter larger than an inner radius), and a thickness of about 50 micrometers.

The substrate may be adhered to the polymeric material by an adhesive. However, too much adhesive may result in the excess adhesive obstructing the viewing area of the eye-mountable device, thereby creating an optical defect. Further, excess adhesive may obstruct and inhibit the electronic components of the eye-mountable device. Therefore, a precise method for adhering the substrate to the polymeric material may be desirable.

In one embodiment, a thin layer of adhesive may be sprayed on one surface of the substrate, and the polymeric material and the substrate may then be pressed together and cured. In one example, the layer of adhesive may be less than about 5 microns. The polymeric material and the adhesive on the substrate may be cured thermally, with ultra-violet light, or photo-cured, as examples. In another embodiment, a thin layer of adhesive may be sprayed on the polymeric material, and the substrate may then be pressed onto the polymeric material. The combined substrate and polymeric material may then be cured, as described above.

In yet another embodiment, a thin layer of adhesive may be stamped onto the polymeric material and/or the substrate with a polydimethylsiloxane (PDMS) stamp. The substrate and the polymeric material may then be pressed together, and cured as described above.

As used throughout this disclosure, the anterior side of the eye-mountable device refers to an outward-facing side of the eye-mountable device, whereas the posterior side of the eye-mountable device refers to an inward-facing side of the eye-mountable device. In particular, when the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

It should be understood that the above examples of the method are provided for illustrative purposes, and should not be construed as limiting.

II. EXAMPLE SYSTEMS AND DEVICES

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc. to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130. The substrate 130 can be a relatively rigid material, such as polyethylene terephthalate ("PET") or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display driver instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOD") proximal to the working electrode can catalyze glucose into hydrogen peroxide ($H_2O_2$). The hydrogen peroxide can then be oxidized at the working electrode, which releases electrons to the working electrode, resulting in an amperometric current that can be measured through the working electrode.

$$glucose + O_2 \xrightarrow{G \rightarrow OD} H_2O_2 + gluconolactone$$

$$H_2O_2 \rightarrow 2H^+ + O_2 + 2e^-$$

The current generated by either reduction or oxidation reactions is approximately proportional to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportional to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 2A:
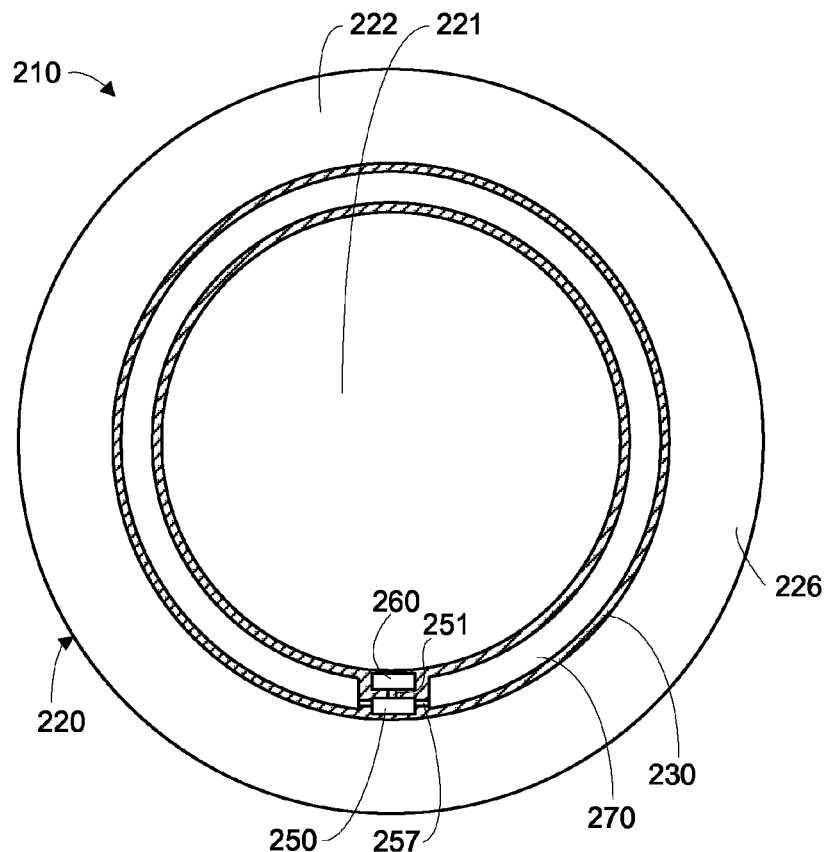
FIG. 2A is a bottom view of an example eye-mountable device.
Figure 2B:
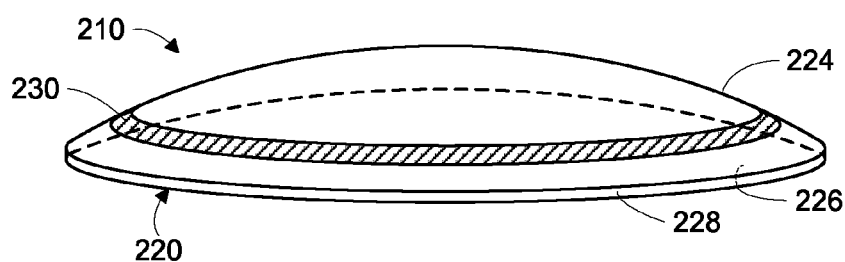
FIG. 2B is an aspect view of the example eye-mountable device shown in FIG. 2A.

FIG. 2A is a bottom view of an example eye-mountable device 210. FIG. 2B is an aspect view of the example eye-mountable device 210. It is noted that relative dimensions in FIGS. 2A and 2B are not necessarily to scale, but have been rendered for purposes of explanation only in describing the arrangement of the example eye-mountable device 210.

The eye-mountable device 210 may include a polymeric material 220, which may be a substantially transparent material to allow incident light to be transmitted to the eye. The polymeric material 220 may include one or more bio-compatible materials similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, or any combinations of these. Other polymeric materials may also be envisioned. The polymeric material 220 may include materials configured to moisturize the corneal surface, such as hydrogels and the like. In some embodiments, the polymeric material 220 is a deformable ("non-rigid") material to enhance wearer comfort.

To facilitate contact-mounting, the eye-mountable device 210 may comprise a concave surface 226 configured to adhere ("mount") to a moistened corneal surface (e.g., by capillary forces with a tear film coating the corneal surface). The bottom view in FIG. 2A faces the concave surface 226. While mounted with the concave surface against the eye, a convex surface 224 of eye-mountable device 210 is formed so as not to interfere with eye-lid motion while the eye-mountable device 210 is mounted to the eye. From the bottom view shown in FIG. 2A, an outer periphery 222, near the outer circumference of the eye-mountable device 210 has a concave curve shape, whereas a central region 221, near the center of the eye-mountable device 210, has a convex curve shape.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 may be selected according to the size and/or shape of the corneal surface of the wearer's eye. In some embodiments, the eye-mountable device 210 is shaped to provide a predetermined, vision-correcting optical power, such as provided by a prescription contact lens.

A sensing platform 230 is embedded in the eye-mountable device 210. The sensing platform 230 can be embedded to be situated near or along the outer periphery 222, away from the central region 221. Such a position ensures that the sensing platform 230 will not interfere with a wearer's vision when the eye-mountable device 210 is mounted on a wearer's eye, because it is positioned away from the central region 221 where incident light is transmitted to the eye-sensing portions of the eye. Moreover, portions of the sensing platform 230 can be formed of a transparent material to further mitigate effects on visual perception.

The sensing platform 230 may be shaped as a flat, circular ring (e.g., a disk with a centered hole). The flat surface of the sensing platform 230 (e.g., along the radial width) allows for mounting electronics such as chips (e.g., via flip-chip mounting) and for patterning conductive materials to form electrodes, antenna(e), and/or interconnections. The sensing platform 230 and the polymeric material 220 may be approximately cylindrically symmetric about a common central axis. The sensing platform 230 may have, for example, a diameter of about 10 millimeters, a radial width of about 1 millimeter (e.g., an outer radius 1 millimeter greater than an inner radius), and a thickness of about 50 micrometers. These dimensions are provided for example purposes only, and in no way limit the present disclosure.

A loop antenna 270, controller 250, and bio-interactive electronics 260 are included in the sensing platform 230. The controller 250 may be a chip including logic elements configured to operate the bio-interactive electronics 260 and the loop antenna 270, and may be the same as or similar to the controller 150 discussed in connection with FIG. 1. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) may be formed from any type of conductive material and may be patterned by any process that be used for patterning such materials, such as deposition or photo-lithography, for example. The conductive materials patterned on the substrate 230 may be, for example, gold, platinum, palladium, titanium, carbon, aluminum, copper, silver, silver-chloride, conductors formed from noble materials, metals, or any combinations of these materials. Other materials may also be envisioned.

Figure 2D:
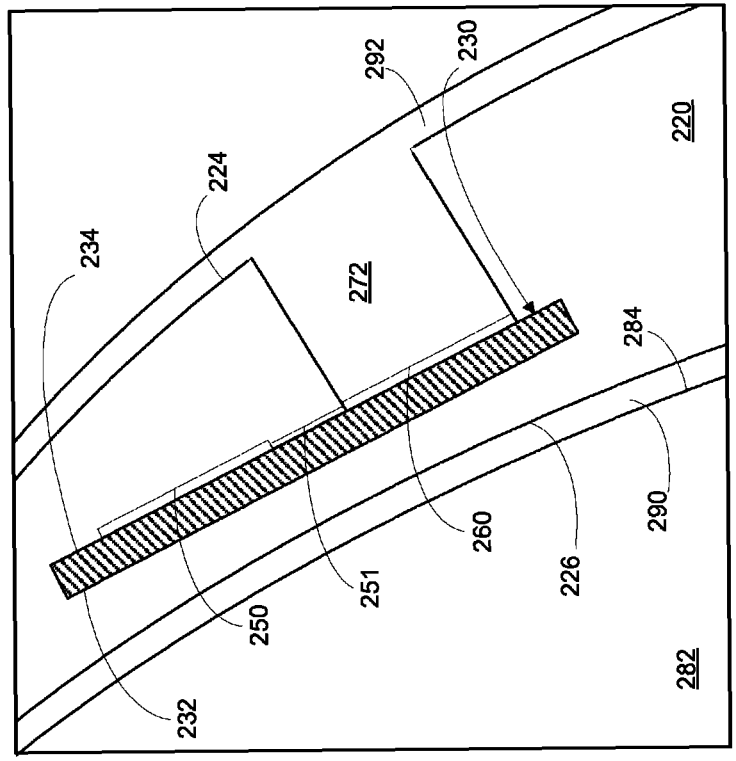
FIG. 2D is a side cross-section view enhanced to show the tear film layers surrounding the surfaces of the example eye-mountable device when mounted as shown in FIG. 2C.

As shown in FIG. 2A, the bio-interactive electronics module 260 is on a side of the sensing platform 230 facing the convex surface 224. Where the bio-interactive electronics module 260 includes an analyte bio-sensor, for example, mounting such a bio-sensor on the sensing platform 230 to be close to the convex surface 224 allows the bio-sensor to sense analyte that has diffused through convex surface 224 or has reached the bio-sensor through a channel in the convex surface 224 (FIGS. 2C and 2D show a channel 272).

The loop antenna 270 is a layer of conductive material patterned along the flat surface of the substrate 230 to form a flat conductive ring. The loop antenna 270 may be the same as or similar to the antenna 170 described in connection with FIG. 1. In some example embodiments, the loop antenna 270 does not form a complete loop. For example, the loop antenna 270 may include a cutout to allow room for the controller 250 and bio-interactive electronics 260, as illustrated in FIG. 2A. However, in another example embodiment, the loop antenna 270 can be arranged as a continuous strip of conductive material that wraps entirely around the sensing platform 230 one or more times. Interconnects between the ends of such a wound antenna (e.g., the antenna leads) can connect to the controller 250 in the sensing platform 230.

The sensing platform 230 may be a bio-compatible structure in which some or all of the components are encapsulated by a bio-compatible material. In one example, controller 250, interconnects 251, 257, bio-interactive electronics 260, and antenna 270 are fully encapsulated by bio-compatible material, except for the sensor electrodes in the bio-interactive electronics 260.

Figure 2C:
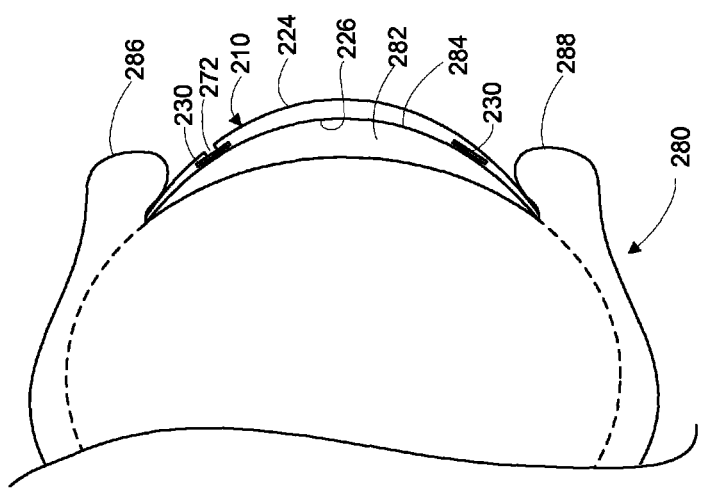
FIG. 2C is a side cross-section view of the example eye-mountable device shown in FIGS. 2A and 2B while mounted to a corneal surface of an eye.

FIG. 2C is a side cross-section view of the example eye-mountable electronic device 210 mounted to a corneal surface 284 of an eye 280. FIG. 2D is an enlarged partial view the cross-section of the example eye-mountable device shown in FIG. 2C. It is noted that relative dimensions in FIGS. 2C and 2D are not necessarily to scale, but have been rendered for purposes of explanation only in describing the arrangement of the example eye-mountable electronic device 210. Some aspects are exaggerated to allow for illustration and to facilitate explanation.

The eye 280 includes a cornea 282 that is covered by bringing an upper eyelid 286 and a lower eyelid 288 together over the surface of the eye 280. Incident light is received by the eye 280 through the cornea 282, where light is optically directed to light sensing elements of the eye 280 to stimulate visual perception. The motion of the upper and lower eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the concave and convex surfaces 224, 226, providing an inner layer 290 (along the concave surface 226) and an outer layer 292 (along the convex surface 224). The inner layer 290 on the corneal surface 284 also facilitates mounting the eye-mountable device 210 by capillary forces between the concave surface 226 and the corneal surface 284. In some embodiments, the eye-mountable device 210 can also be held over the eye 280 in part by vacuum forces against the corneal surface 284 due to the curvature of the concave surface 226. The tear film layers 290, 292 may be about 10 micrometers in thickness and together account for about 10 microliters of fluid.

The tear film is in contact with the blood supply through capillaries in the structure of the eye and includes many biomarkers found in blood that are analyzed to diagnose health states of an individual. For example, tear film includes glucose, calcium, sodium, cholesterol, potassium, other biomarkers, etc. The biomarker concentrations in tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body.

As shown in the cross-sectional views in FIGS. 2C and 2D, the sensing platform 230 can be inclined so as to be approximately parallel to the adjacent portion of the convex surface 224. As described above, the sensing platform 230 is a flattened ring with an inward-facing surface 232 (closer to the concave surface 226 of the polymeric material 220) and an outward-facing surface 234 (closer to the convex surface 224). The sensing platform 230 can include electronic components and/or patterned conductive materials adjacent to either or both surfaces 232, 234.

As shown in FIG. 2D, the bio-interactive electronics 260, the controller 250, and the conductive interconnect 251 are mounted on the outward-facing surface 234 such that the bio-interactive electronics 260 are facing the convex surface 224. With this arrangement, the bio-interactive electronics 260 can receive analyte concentrations in the tear film 292 through the channel 272. However, in other examples, the bio-interactive electronics 260 may be mounted on the inward-facing surface 232 of the sensing platform 230 such that the bio-interactive electronics 260 are facing the concave surface 226.

III. AN OPHTHALMIC ELECTROCHEMICAL ANALYTE SENSOR

Figure 3:
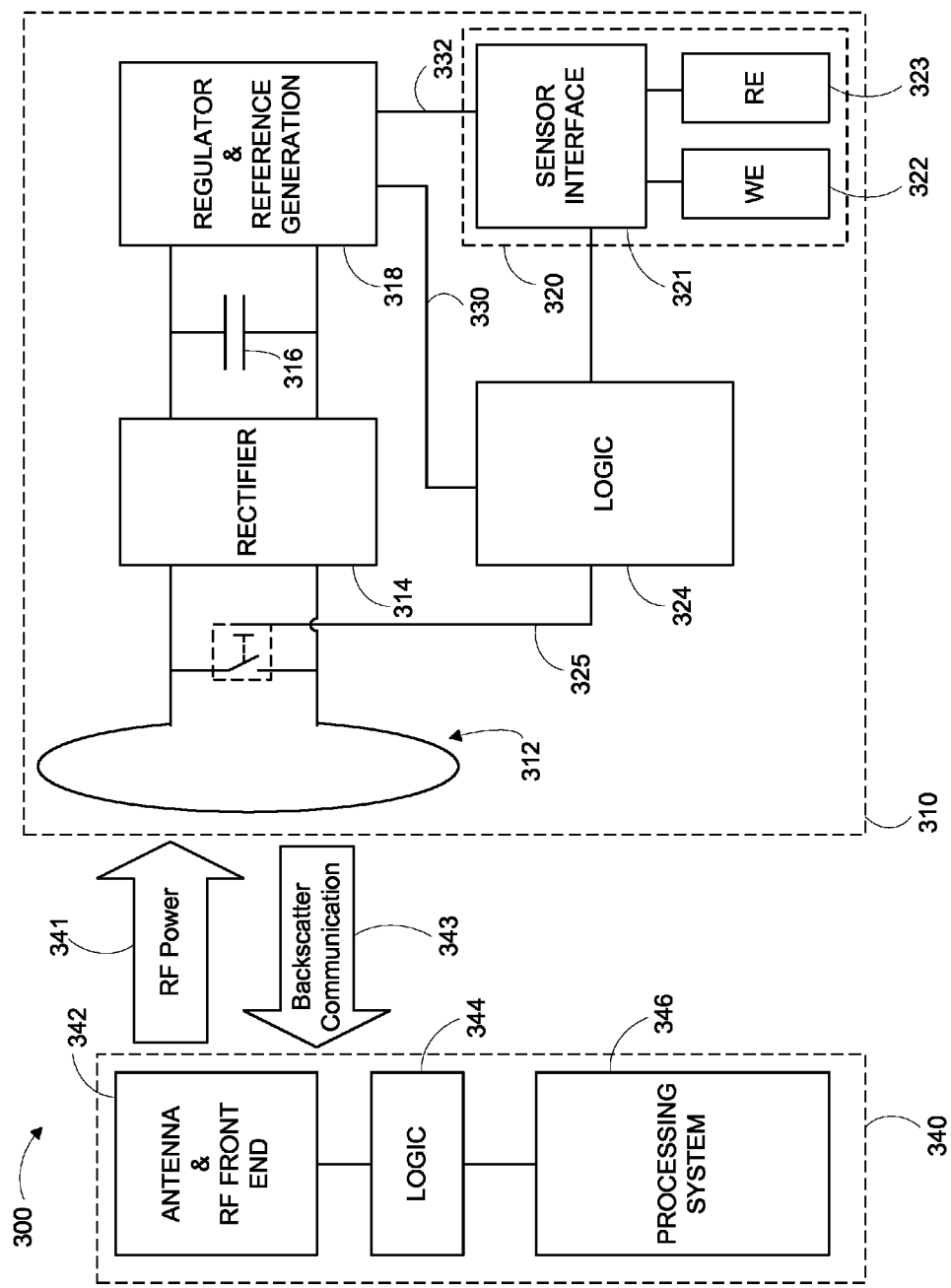
FIG. 3 is a functional block diagram of an example system for electrochemically monitoring a tear film analyte concentration.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating (325) the impedance of the antenna 312. Similar to the eye-mountable devices 110, 210 discussed above in connection with FIGS. 1 and 2, the eye-mountable device 310 can include a mounting substrate embedded within a polymeric material configured to be mounted to an eye. The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter high frequency noise on the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or a network-connected memory.

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
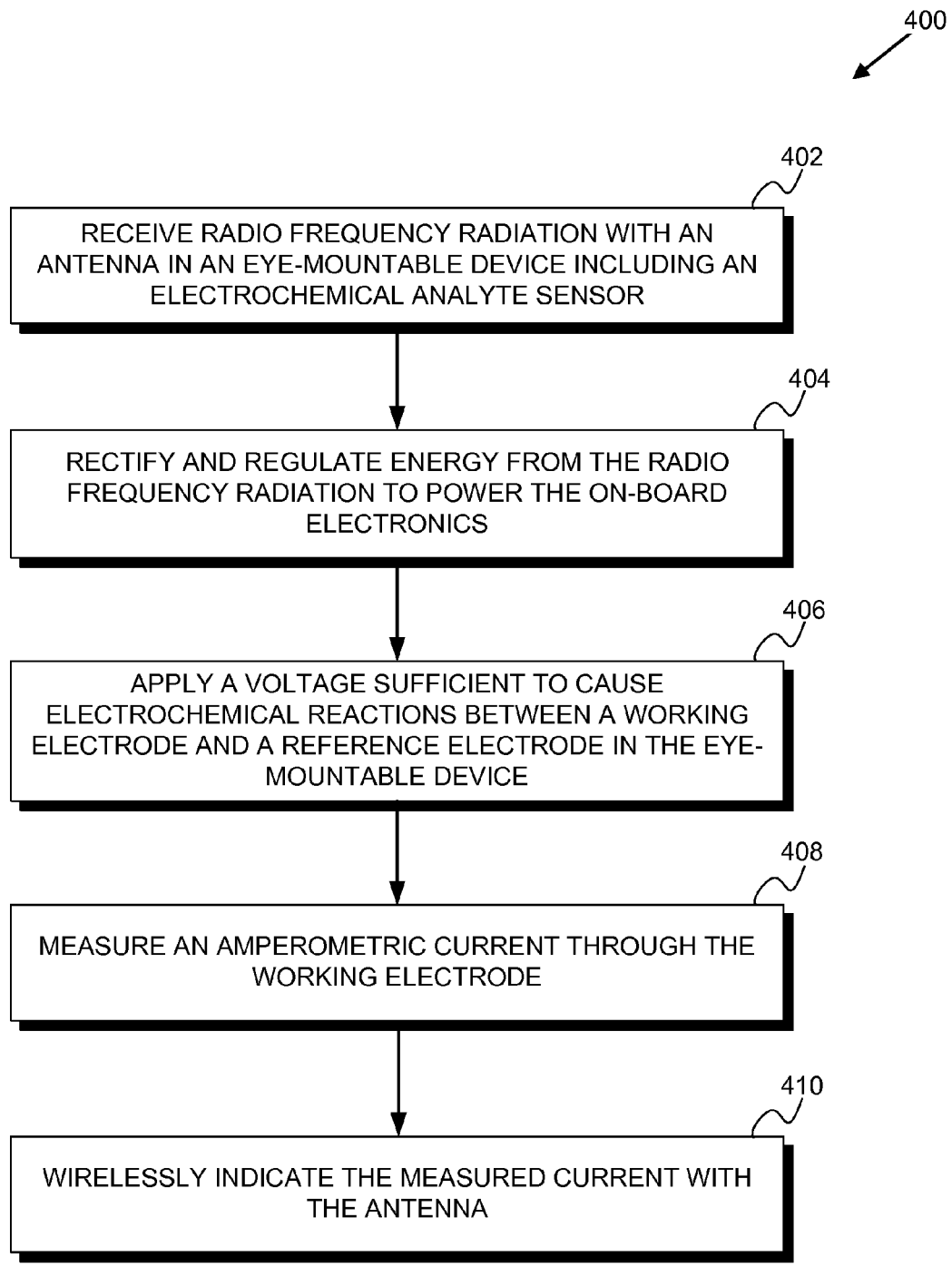
FIG. 4A is a flowchart of an example process for operating an amperometric sensor in an eye-mountable device to measure a tear film analyte concentration.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
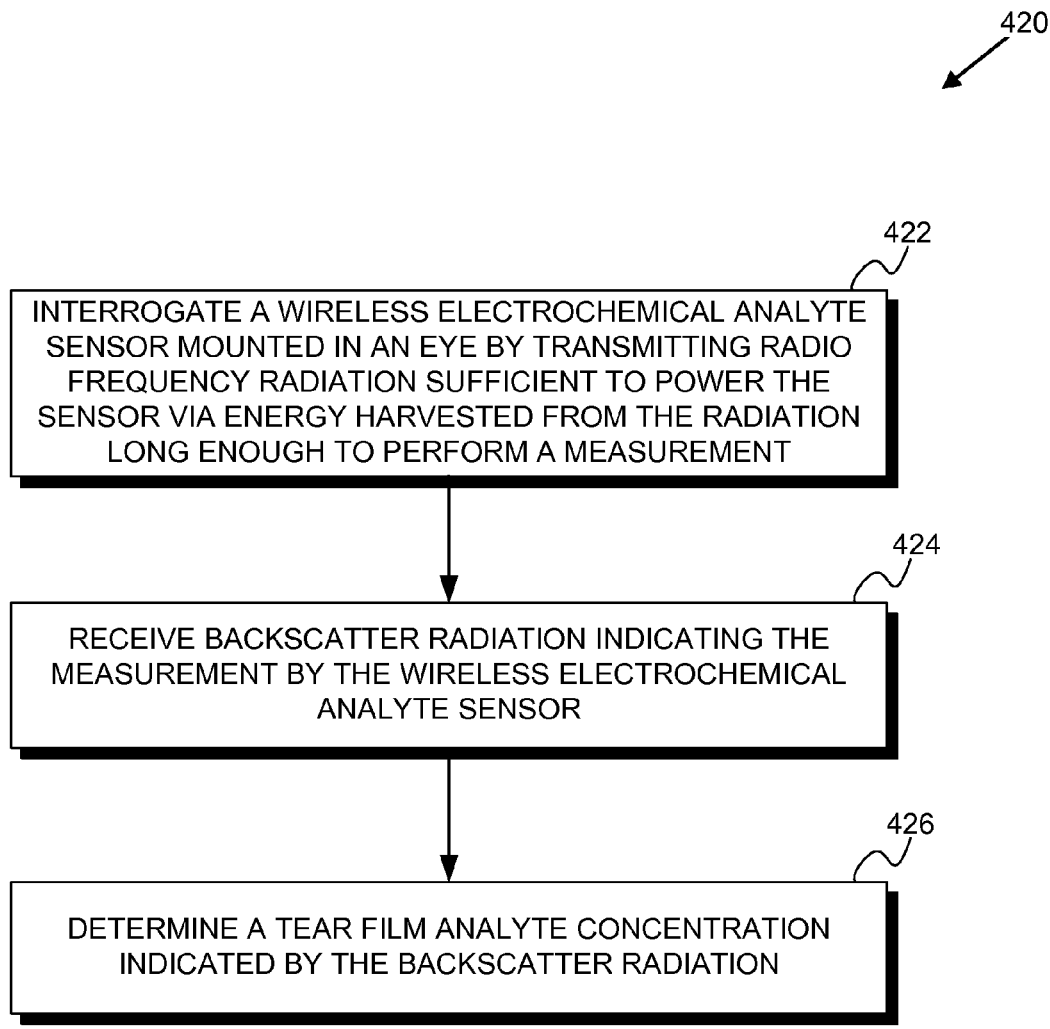
FIG. 4B is a flowchart of an example process for operating an external reader to interrogate an amperometric sensor in an eye-mountable device to measure a tear film analyte concentration.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

While the body-mountable device has been described as comprising the eye-mountable device 110, 210, 310, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

IV. EXAMPLE METHODS

As discussed above, an eye-mountable device may include a first polymer layer defining a first side of the eye-mountable device, and a second layer defining a second side of the eye-mountable device. A substrate may be embedded between the first and second polymer layers to provide a mounting surface for electronic components of the eye-mountable device. The substrate may be adhered to the polymeric material by an adhesive. However, too much adhesive may result in the excess adhesive obstructing the viewing area of the eye-mountable device, thereby creating an optical defect. Further, excess adhesive may obstruct and inhibit the electronic components of the eye-mountable device. Therefore, a more precise method for adhering the substrate to the polymeric material may be desirable.

Figure 5:
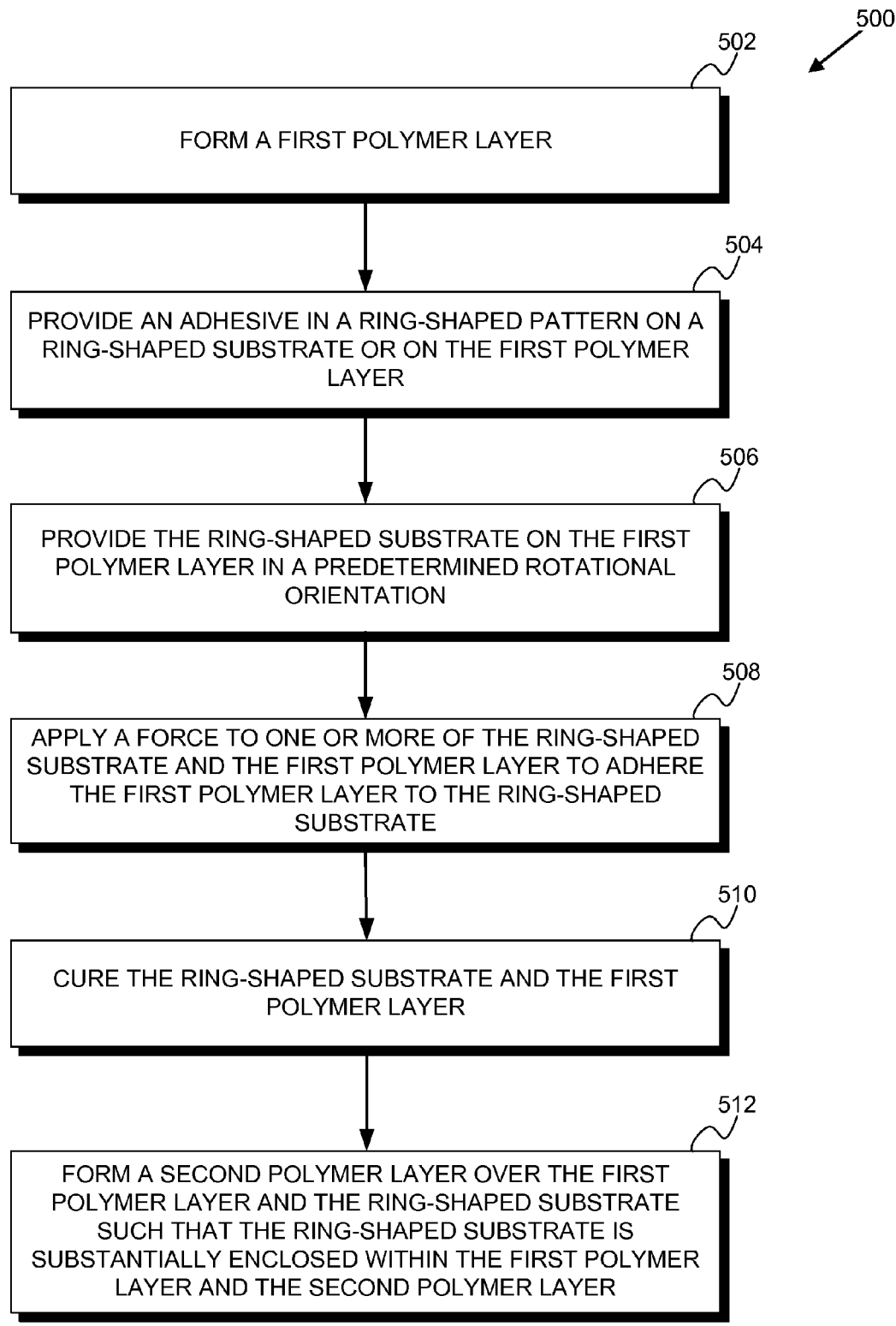
FIG. 5 is a flowchart illustrating a method, according to an exemplary embodiment.

FIG. 5 is a flow chart of a method 500 for adhering a substrate to a polymeric material. The method 500 may include one or more operations, functions, or actions as illustrated by one or more of blocks 502-512. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

For purposes of illustration, the method is described below in a scenario where a body-mountable device comprises an eye-mountable device. It should be understood, however, that the method 500 may involve scenarios where the body-mountable device comprises other mountable devices that are mounted to other portions of the human body. For example, method 500 may involve scenarios where the body-mountable device comprises a tooth-mountable device and/or a skin mountable device.

At block 502, the method may include forming a first polymer layer. An example fabrication device may be used to form the first polymer layer. FIG. 6A illustrates an example fabrication device 600 that includes example molding pieces that may be used to form the first polymer layer. The fabrication device 600 may include a first molding piece 602 and a second molding piece 604. The first molding piece 602 and the second molding piece 604 may define a first cavity. The second molding piece 604 may be filled with a polymeric material 606, and the polymeric material 606 may be compressed into a first polymer layer 608 by the first molding piece 602.

The first molding piece 602 and the second molding piece 604 may be configured to achieve a given desired thickness of the first polymer layer 608. For instance, in an example, the first polymer layer 608 can have a thickness of less than 150 micrometers. In an example embodiment, the first molding piece 602 and the second molding piece 604 can be designed so as to allow for a layer having less than a 150 micrometer thickness between the two cavities. As such, when the first molding piece 602 and the second molding piece 604 are pressed together during the formation of the first polymer layer 608, the resulting polymer layer will have a thickness of less than 150 micrometers.

In an example, the thickness of the first polymer layer 608 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

The first polymer layer 608 may include a polymeric material containing polymerizable monomers, such as those commonly used in hydrogels, silicone hydrogels, silicone elastomers, and rigid gas permeable materials. Further, the polymeric material may form a transparent or substantially transparent polymer layer. As such, the use of the polymeric material may result in an eye-mountable device through which the wearer can see when mounted on the wearer's eye. In an example, the polymeric material can be a hydrogel material, such as a silicone hydrogel or can be a non-hydrogel, such as a silicone elastomer. Other materials are possible as well.

The first polymer layer 608 may define a posterior side 610 of an eye-mountable device. That is, the first polymer layer 608 may define an outer edge of the eye-mountable device. When mounted on an eye of a user, the posterior side 610 of the eye-mountable device defined by the first polymer layer 608 corresponds to a side of the device touching the eye of the user. The first molding piece 602 may be shaped so as to define a shape of the posterior side 610. For example, a curvature of the posterior side 610 may be defined by the first molding piece 602.

Other methods for forming first polymer layer are possible as well. For example, the first polymer layer may be formed via injection molding. In injection molding, rather than monomers being cured between molding pieces, polymeric molding material may be heated and injected or otherwise forced into a molding piece or pieces. The injected polymeric molding material may then cool and harden to the configuration of the molding piece or pieces.

As another example, the first polymer layer may be formed via spin casting. Through spin-casting techniques, the fabrication device may form a first polymer layer of a precise thickness. In an example, a spin-casting mold may be spun along its central access at a set speed, and the polymer or monomer formulation may be introduced to the mold as the mold is spinning in order to form a first polymer layer. This first polymer layer may then be cured. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

At block 504, the method may include providing an adhesive in a ring-shaped pattern on a ring-shaped substrate or on the first polymer layer. FIGS. 6B and 6C illustrate example adhesive provided in a ring-shaped pattern. The ring-shaped substrate 614 may have a radial width dimension sufficient to provide a mounting platform for electronics components. The ring-shaped substrate 614 may have a thickness sufficiently small to allow the ring-shaped substrate 614 to be embedded within two layers of polymeric material comprising an eye-mountable device. The substrate may be a relatively rigid polymeric material, such as polyethylene terephthalate ("PET"), paralyene or another material sufficient to structurally support circuitry and/or electronics. The ring-shaped substrate 614 may have a thickness sufficiently large to provide structural stability suitable for supporting electronic components mounted thereon. For example, the ring-shaped substrate 614 may have a diameter of about 10 millimeters, a radial width of about 1 millimeter (e.g., an outer radius 1 millimeter larger than an inner radius), and a thickness of about 50 micrometers. Other examples are possible as well.

During fabrication of an eye-mountable device, it may be desirable for the ring-shaped substrate 614 to remain in a fixed position during fabrication of the eye-mountable device. For instance, movement of the ring-shaped substrate 614 during subsequent formation steps, such as formation of a second polymer layer, may result in improper placement of the ring-shaped substrate 614 relative to the surrounding polymer layers. As one example, movement of the ring-shaped substrate 614 during filling a mold piece with a polymeric material to form the second polymer layer and/or curing the second polymer layer can result in improper placement of the ring-shaped substrate 614 relative to the surrounding polymer layers.

Therefore, in an example, an adhesive 616 is applied to the ring-shaped substrate 614 and/or the first polymer layer 608 before the ring-shaped substrate 614 is placed on the first polymer layer 608. The applied adhesive 616 may facilitate adhesion of the ring-shaped substrate 614 to the first polymer layer 608. For instance, a small amount of adhesive 616 may be applied to the first polymer layer 608, and the ring-shaped substrate 614 may be positioned on the small amount of adhesive 616 such that the ring-shaped substrate 614 adheres to the first polymer layer 608. FIG. 6B illustrates such an embodiment. Additionally or alternatively, a small amount of adhesive 616 may be applied to the ring-shaped substrate 614, and the ring-shaped substrate 614 may then be placed on the first polymer layer 608 such that the ring-shaped substrate 614 adheres to the first polymer layer 608. FIG. 6C illustrates such an embodiment. With this arrangement, the ring-shaped substrate 614 may remain adhered to the first polymer layer 608 in a secure location during subsequent formation steps. The adhesive 616 may include a silicone resin, as an example. In other examples the adhesive can be the same or different than the biocompatible materials that form the polymer layers.

In an example, an optically clear silicone elastomer (such as NuSil MED-6020, as an example) may be used to form the first polymer layer 608. In a second step, a fast cured silicone adhesive (such as NuSil MED 3-4013, as an example) in xylene may be spray coated onto one side of the ring-shaped substrate 614. The ring shaped substrate may then be placed on the first polymer layer 608 and a force is applied while heated curing the silicone adhesive.

In yet another example, an optically clear silicone elastomer (such as NuSil MED-6020, as an example) may be used to form the first polymer layer 608. A photocurable silicone adhesive that may contain M2D50 (such as α,ω-dimethacrylated polydimethylsiloxane, as an example) and Darocur 1173 is stamped onto the first polymer layer in the shape of the ring shaped substrate 614. The ring shaped substrate may then be placed onto the first polymer layer 608 and a force is applied while curing with UV light.

A wide variety of adhesives may be utilized and generally include monomers or macromonomers that can be cured thermally, or by UV or visible light. Additionally, thermoplastic adhesives can be utilized that are heated and the adhesion is set in upon cooling of the ringed substrate 614 and first polymer layer 608.

In one embodiment, the adhesive 616 may be sprayed on the ring-shaped substrate 614 and/or the first polymer layer 608. Spraying the adhesive 616 may be advantageous to brushing the adhesive 616 since brushing may result in a thicker adhesive layer than spraying. Typical brushing may result in an adhesive layer of about 30 micrometers, while spraying the adhesive may result in a thickness of less than about 5 micrometers. Additionally, spraying the adhesive may result in a more uniform adhesive layer than brushing. A smaller amount and more uniform distribution of the adhesive 616 may minimize spreading of the adhesive 616 onto the electronic components mounted on the ring-shaped substrate 614 or into the viewing area of the eye-mountable device.

In one example, the adhesive 616 may be sprayed on the ring-shaped substrate 614 and/or the first polymer layer 608 in a ring-shaped pattern using a nebulizer. The nebulizer may be configured to spray a ring-shaped pattern of adhesive 616 having an outer diameter a few millimeters smaller than the ring-shaped substrate 614, and an inner diameter a few millimeters larger than the ring-shaped substrate 614. The nebulizer may be controlled by a robotics system, configured to position the nebulizer in a precise location to spray the adhesive 616 on the ring-shaped substrate 614 and/or the first polymer layer 608 in a ring-shaped pattern. Other embodiments are possible as well.

In another embodiment, the adhesive 616 may be stamped on the ring-shaped substrate 614 and/or the first polymer layer 608. Stamping the adhesive 616 may be advantageous to brushing the adhesive 616 since brushing may result in a thicker adhesive layer than stamping. Typical brushing may result in an adhesive layer of about 30 micrometers, while stamping the adhesive may result of a thickness of only a few micrometers. Additionally, stamping the adhesive may result in a more uniform adhesive layer than brushing. These advantages may prevent the adhesive 616 from spreading onto the electronic components mounted on the ring-shaped substrate 614 or into the viewing area of the eye-mountable device.

In one example, the adhesive 616 may be stamped on the ring-shaped substrate 614 and/or the first polymer layer 608 in a ring-shaped pattern using a polydimethylsiloxane (PDMS) stamp. The PDMS stamp may be ring-shaped, with an outer diameter a few millimeters smaller than the ring-shaped substrate, and an inner diameter a few millimeters larger than the ring-shaped substrate. In one example, a pad containing the adhesive 616 may be stamped by the PDMS stamp, thereby transferring a small amount of adhesive 616 from the pad to the PDMS stamp. The PDMS stamp containing the adhesive 616 may then be stamped on the ring-shaped substrate 614 and/or the first polymer layer 608, thereby transferring a thin layer of adhesive 616 to the ring-shaped substrate 614 and/or the first polymer layer 608. In one example, the PDMS stamp may be controlled by a robotics system. Other embodiments are possible as well.

Figure 6D:
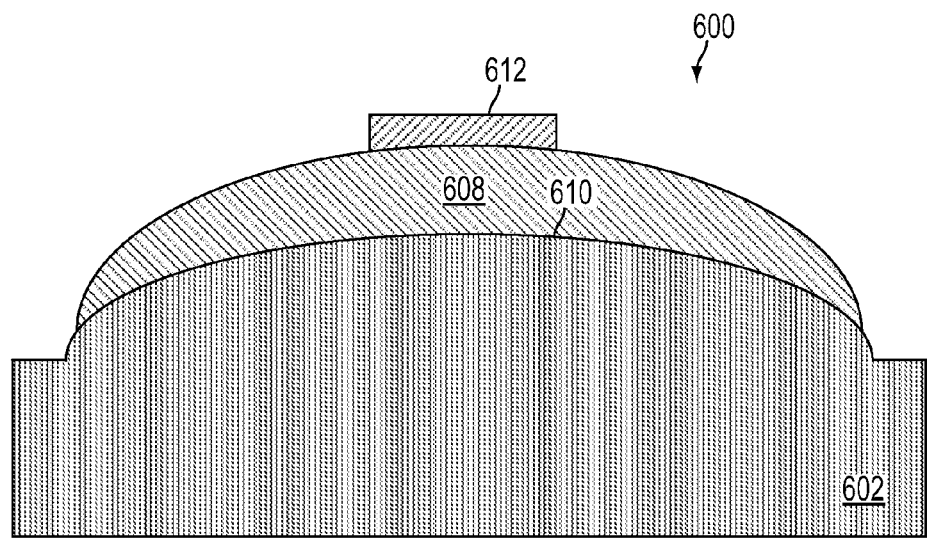
FIG. 6D is an illustration of positioning a ring-shaped structure on a first polymer layer in a predetermined rotational orientation, according to an example embodiment.
Figure 6E:
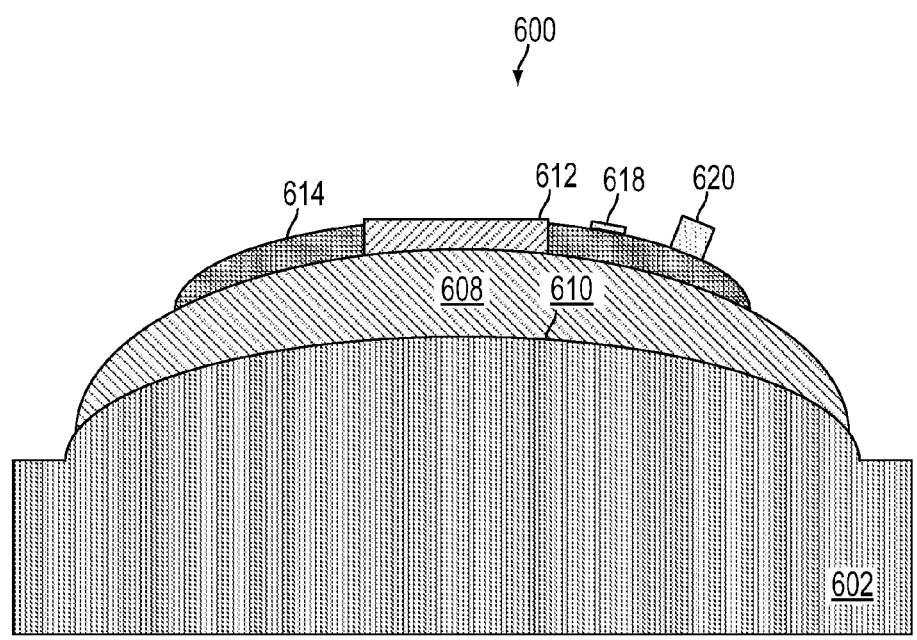
FIG. 6E is an illustration of positioning a ring-shaped structure on a first polymer layer in a predetermined rotational orientation, according to an example embodiment.

At block 506, the method may include providing the ring-shaped substrate on the first polymer layer in a predetermined rotational orientation. FIGS. 6D and 6E illustrate an example in which the ring-shaped substrate 614 is positioned on the first polymer layer 608 in a predetermined rotational orientation. The ring-shaped substrate 614 may occupy a peripheral portion of the eye-mountable device so as to limit interference with a user's field of view when the eye-mountable device is mounted on an eye of the user. The ring-shaped structure 614 can further include a sensor 618 and electronics 620 that are each mounted thereon. In some examples, the ring-shaped substrate 614 may be more rigid than the first polymer layer 608. In order to position the ring-shaped substrate 614, example fabrication device 600 may separate the first molding piece 602 from the second molding piece 604. When the fabrication device 600 separates the first molding piece 602 from the second molding piece 604, the first polymer layer 608 may stick to a side of the first molding piece 602. In an example, the first polymer layer 608 and/or the first molding piece 602 can be surface treated, such that the first polymer layer 608 sticks to the side of the first molding piece 602. Additionally or alternatively, the second molding piece 604 can be surface treated, such that the first polymer layer 608 sticks to the side of the first molding piece 602.

In an example, positioning the ring-shaped substrate 614 on the first polymer layer 608 in a predetermined rotational orientation can include aligning the ring-shaped structure 614 with an alignment feature 612. In one example, there may be a hole in the ring-shaped substrate 614 that has an asymmetric inner diameter and the alignment feature may include an asymmetric peg such that the hole receives the alignment feature 612 in only the predetermined rotational orientation. However, other ways of providing the predetermined rotational orientation of the ring-shaped structure 614 by alignment with an alignment feature 612 are also possible.

Alternatively, the example fabrication device 600 may include a positioning apparatus, such as a robotic system, configured to position the ring-shaped substrate 614 on the first polymer layer 608 in a predetermined rotational orientation. For instance, the positioning apparatus may (i) pick up the ring-shaped substrate 614 (e.g., via suction), (ii) position the ring-shaped substrate 614 above the first polymer layer 608, and then (iii) lower the ring-shaped substrate 614 toward the first polymer layer 608. When the ring-shaped substrate 614 is positioned in the predetermined rotational orientation, the positioning apparatus may then release the ring-shaped substrate 614 (e.g., by releasing the suction). With this approach, the first polymer layer 608 might not include an alignment feature 612.

The positioning apparatus may further include a vision system configured to assist with positioning the ring-shaped substrate 614 on the first polymer layer 608 in a predetermined rotational orientation. Such a vision system may facilitate guiding the ring-shaped substrate 614 to a precise location on the first polymer layer 608. In an example, the vision system can be appropriate for situations in which one or more production specifications for an eye-mountable device, such as example eye-mountable device 110, have requirements with very low tolerances related to the positioning of a sensor, such as sensor 618, within the eye-mountable device.

At block 508, the method may include applying a force to one or more of the ring-shaped substrate and the polymer layer to adhere the first polymer layer to the ring-shaped substrate. In one embodiment, the positioning apparatus described above may apply the force to the ring-shaped substrate. For instance, the positioning apparatus may (i) pick up the ring-shaped substrate (e.g., via suction), (ii) position the ring-shaped substrate above the first polymer layer, (iii) lower the ring-shaped substrate toward the first polymer layer, and then (iv) apply a force to the ring-shaped substrate to adhere the first polymer layer to the ring-shaped substrate. In another example, the ring-shaped substrate may be positioned by a first apparatus, and a second apparatus may apply the force to the ring-shaped substrate. Other examples are possible as well.

At block 510, the method may include curing the ring-shaped substrate and the first polymer layer. Curing involves the hardening of a polymeric material by cross-linking of polymer chains, and curing may be, for example, brought about by chemical additives, ultraviolet radiation, electron beam, and/or heat. In an example, the polymeric material can be a light-curable polymeric material, and the fabrication device may be configured to cure the light-curable polymeric material using light, such as ultraviolet light or visible light. Other examples are possible as well.

Figure 6F:
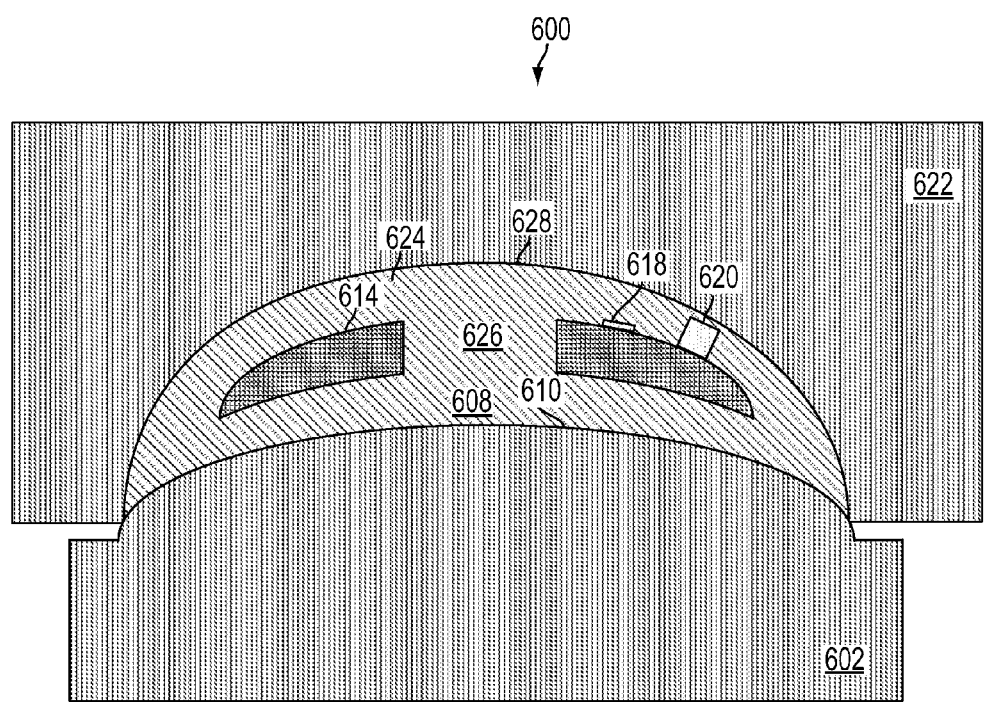
FIG. 6F is an illustration of formation of a second polymer layer, according to an example embodiment.

At block 512, the method may include forming a second polymer layer over the first polymer layer and the ring-shaped substrate such that the ring-shaped substrate is substantially enclosed within the first polymer layer and the second polymer layer. FIG. 6F illustrates example fabrication device 600 including example molding pieces that may be used to form the second polymer layer. The first molding piece 602, which holds the first polymer layer 608 to which the ring-shaped substrate 614 is adhered, may be filled with a polymeric material 624. The polymeric material 624 may be formed into a second polymer layer 626 by compression between the first molding piece 602 and a third molding piece 622. As a result, the second polymer layer 626 may mold over the ring-shaped substrate 614, such that the ring-shaped substrate 614 is at least partially enclosed by the first polymer layer 608 and the second polymer layer 626.

After the second polymer layer 626 is formed, example fabrication device 600 may cure the second polymer layer 626. In an example, the second polymer layer 626 can be cured like the first polymer layer 608. However, in other examples, the second polymer layer 626 may be cured by different techniques than the first polymer layer 608. The second polymer layer 626 can be cured by any of the techniques mentioned herein. In an example, the fabrication device 600 may cure the first polymer layer 608 at this stage.

The first molding piece 602 and the third molding piece 622 may be configured to achieve a given desired thickness of a layer formed between the two pieces. As one example, the first molding piece 602 and the third molding piece 622 may be designed so as to define a thickness of the second polymer layer 626. As another example, the first molding piece 602 and the third molding piece 622 may be designed so as to define a final thickness of an eye-mountable device. In an example, the first molding piece 602 and the third molding piece 622 can be designed so as to allow for a layer having a given desired thickness between the two pieces (in addition to a thickness of the first polymer 608). As such, when the first molding piece 602 and the third molding piece 622 are pressed together during formation of a layer, the resulting layer will have the given desired thickness.

In an example, the second polymer layer 626 has a thickness of greater than 50 micrometers. However, in other examples, the second polymer layer 626 can have a thickness between 50 and 300 micrometers, such as 130 micrometers. It should be understood that since the second polymer layer 626 molds over the ring-shaped substrate 614, the second polymer layer 626 may not have a uniform thickness. In an example, the thickness of the second polymer layer 626 can be selected based on a particular analyte or analytes that the eye-mountable device is configured to detect. For example, an optimal thickness for a first analyte may be 10 micrometers, while an optimal thickness for a second analyte may be 25 micrometers. Other examples are possible as well.

In an example, the second polymer layer 626 can be composed of the same polymeric material as the first polymer layer 608. However, in other examples, the second polymer layer 626 can be composed of a different polymeric material than the first polymer layer 608. The second polymer layer 626 can be any one of the polymeric materials mentioned herein. In an example, the ring-shaped substrate 614 may be more rigid than the second polymer layer 626.

The second polymer layer 626 may define an anterior side 628 of an eye-mountable device. That is, the second polymer layer 626 defines an outer edge of the eye-mountable device. When mounted on an eye of a user, the anterior side 628 of the eye-mountable device defined by the second polymer layer 626 corresponds to the side of the device that is not touching the eye of the user. The third molding piece 622 may be shaped so as to define a shape of the anterior side 628. For example, a curvature of the anterior side 628 may be defined by the third molding piece 622.

Figure 7:
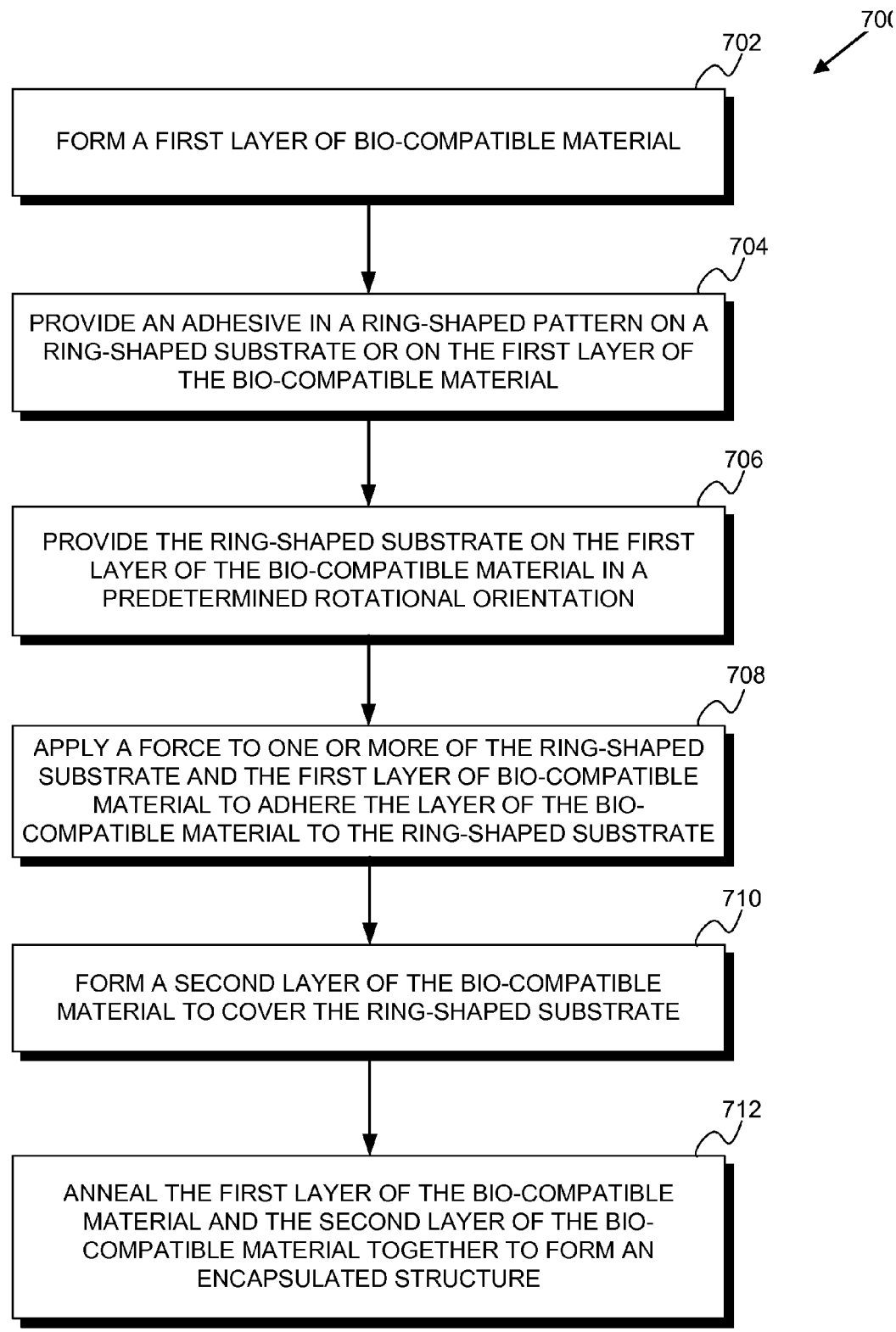
FIG. 7 is a flowchart illustrating another method, according to an exemplary embodiment.

FIG. 7 is a flow chart of another method 700 for adhering a substrate to a bio-compatible material. The method 700 may include one or more operations, functions, or actions as illustrated by one or more of blocks 702-712. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

For purposes of illustration, the method is described below in a scenario where a body-mountable device comprises an eye-mountable device. It should be understood, however, that the method 700 may involve scenarios where the body-mountable device comprises other mountable devices that are mounted to other portions of the human body. For example, method 700 may involve scenarios where the body-mountable device comprises a tooth-mountable device and/or a skin mountable device.

At block 702, the method may include forming a first layer of a bio-compatible material. The first layer of bio-compatible material may include a variety of materials. For example, the first layer of bio-compatible material may include a polymeric material such as SCS parylene-C (e.g., dichlorodi-p-xylylene), a polyethylene terephthalate (PET), a polydimethysiloxane (PDMS), other silicone elastomers, and/or another bio-compatible polymeric material. The term "bio-compatibility," as used in this disclosure, refers generally to the ability of a material or device to co-exist with a biological host. Bio-compatible materials are generally those that do not bring about a host response (such as an immune response) that results in deleterious effects to either the biological host or the material. In addition to being bio-compatible, the first layer of bio-compatible material may be an electrically insulating material to isolate the encapsulated electronics from the surrounding environment (e.g., from current-carrying particles and/or fluids). In an example, the first layer of bio-compatible material may be formed by a microfabrication process such as chemical vapor deposition. Other examples are possible as well.

Moreover, the first layer of bio-compatible material may have a variety of thicknesses. For example, the first layer of bio-compatible material may have a thickness between 5 to 50 micrometers, such as 15 micrometers. Other thicknesses of the first layer of bio-compatible material are possible as well.

At block 704, the method may include providing an adhesive in a ring-shaped pattern on a ring-shaped substrate or on the first layer of bio-compatible material. The ring-shaped substrate may have a radial width dimension sufficient to provide a mounting platform for electronics components. The substrate may be a relatively rigid polymeric material, such as polyethylene terephthalate ("PET"), paralyene or another material sufficient to structurally support circuitry and/or electronics. The ring-shaped substrate may have a thickness sufficiently small to allow the ring-shaped substrate to be embedded within two layers of polymeric material comprising an eye-mountable device. The ring-shaped substrate may have a thickness sufficiently large to provide structural stability suitable for supporting electronic components mounted thereon.

An adhesive may be applied to the ring-shaped substrate and/or the first layer of bio-compatible material before the ring-shaped substrate is placed on the first layer of bio-compatible material. The applied adhesive may facilitate adhesion of the ring-shaped substrate to the first layer of bio-compatible material. For instance, a small amount of adhesive may be applied to the first layer of bio-compatible material, and the ring-shaped substrate may be positioned on the small amount of adhesive such that the ring-shaped substrate adheres to the first layer of bio-compatible material. Additionally or alternatively, a small amount of adhesive may be applied to the ring-shaped substrate, and the ring-shaped substrate may then be placed on the first layer of bio-compatible material such that the ring-shaped substrate adheres to the first layer of bio-compatible material. With this arrangement, the ring-shaped substrate may remain adhered to the first layer of bio-compatible material in a secure location during subsequent formation steps. The adhesive may include a silicone resin, as an example. The adhesive may be sprayed on the ring-shaped substrate and/or the first polymer layer, or the adhesive may be stamped on the ring-shaped substrate and/or the first polymer layer. It should be understood that one or more aspects of block 704 of method 700 may be may be similar to aspects described above with respect to block 504 of method 500. Other examples are possible as well.

At block 706, the method may include providing the ring-shaped substrate on the first layer of the bio-compatible material in a predetermined rotational orientation. In an example, positioning the ring-shaped substrate on the first layer of bio-compatible material in a predetermined rotational orientation can include aligning the ring-shaped structure with an alignment feature. In one example, there may be a hole in the ring-shaped substrate has an asymmetric inner diameter and the alignment feature may include an asymmetric peg such that the hole receives the alignment feature in only the predetermined rotational orientation. However, other ways of providing the predetermined rotational orientation of the ring-shaped structure by alignment with an alignment feature are also possible.

Alternatively, the example fabrication device may include a positioning apparatus, such as a robotic system, configured to position the ring-shaped substrate on the first layer of bio-compatible material in a predetermined rotational orientation. For instance, the positioning apparatus may (i) pick up the ring-shaped substrate (e.g., via suction), (ii) position the ring-shaped substrate above the first layer of bio-compatible material, and then (iii) lower the ring-shaped substrate toward the first layer of bio-compatible material. When the ring-shaped substrate is positioned in the predetermined rotational orientation, the positioning apparatus may then release the ring-shaped substrate (e.g., by releasing the suction). With this approach, the first layer of bio-compatible material might not include an alignment feature. It should be understood that one or more aspects of block 706 of method 700 may be may be similar to aspects described above with respect to block 506 of method 500. Other examples are possible as well.

At block 708, the method may include applying a force to one or more of the ring-shaped substrate and the polymer layer to adhere the first layer of the bio-compatible material to the ring-shaped substrate. In one example, the positioning apparatus described above may apply the force to the ring-shaped substrate. For instance, the positioning apparatus may (i) pick up the ring-shaped substrate, (ii) position the ring-shaped substrate above the first layer of bio-compatible material, (iii) lower the ring-shaped substrate toward the first layer of bio-compatible material, and then (iv) apply a force to the ring-shaped substrate to adhere the first layer of bio-compatible material to the ring-shaped substrate. In another example, the ring-shaped substrate may be positioned by a first apparatus, and a second apparatus may apply the force to the ring-shaped substrate. It should be understood that one or more aspects of block 708 of method 700 may be may be similar to aspects described above with respect to block 508 of method 500. Other examples are possible as well.

At block 710, the method may include forming a second layer of the bio-compatible material to cover the ring-shaped substrate. The second layer of bio-compatible material may be composed of the same polymeric material as the first layer of bio-compatible material. However, in other examples, the second layer of bio-compatible material may be composed of a different polymeric material than the first layer of bio-compatible material. The second layer of bio-compatible material may include any one of the polymeric materials mentioned herein that is both bio-compatible and electrically insulating. The second layer of bio-compatible material may serve to seal and insulate the electronic components mounted on the ring-shaped substrate.

Moreover, the second layer of bio-compatible material may have a variety of thicknesses. For example, the second layer of bio-compatible material may have a thickness between one or more embedded components and a surface of the second layer of bio-compatible material between 5 to 100 micrometers, such as 15 micrometers. Other thicknesses for the second layer of bio-compatible materials are possible as well.

In an example, the second layer of bio-compatible material may be formed the same or similar way as the first layer of bio-compatible material may be formed. However, in other examples, the second layer of bio-compatible material may be formed by a different process (or processes) than the process (or processes) used to form the first layer of bio-compatible material. For example, the second layer of bio-compatible material may be formed by a microfabrication process such as chemical vapor deposition. The deposition of the second layer of bio-compatible material may result in a conformal coating over the assembled components. Other examples are possible as well.

At block 712, the method may include annealing the first layer of the bio-compatible material and the second layer of the bio-compatible material together to form an encapsulated structure. The encapsulated structure may include the ring-shaped substrate fully enclosed between the first layer of the bio-compatible material and the second layer of the bio-compatible material. With this arrangement, the second layer of bio-compatible material may bond to the first layer of bio-compatible material.

The first layer of bio-compatible material and the second layer of bio-compatible material may be annealed together by placing the entire multi-layered structure in an oven heated to a temperature sufficient to anneal the bio-compatible material. Following the annealing, the regions where the two layers of bio-compatible materials were in direct contact, including the outer edges of the electronic components, are sealed together by the annealed bond. The electronic components mounted on the ring-shaped substrate are thereby fully encapsulated by the bio-compatible material. In an example where the bio-compatible material includes parylene (dichlorodi-p-xylylene), the annealing temperature can be a temperature between 150 and 200 degrees Celsius. Other bio-compatible polymeric materials (such as PET, PDMS, etc.) may require higher or lower annealing temperatures.

In one embodiment, the encapsulated structure may be embedded in an eye-mountable device including a transparent polymeric material having a concave surface and a convex surface. The concave surface may be configured to be removably mounted over a corneal surface, and the convex surface may be configured to be compatible with eyelid motion when the concave surface is so mounted. The eye-mountable device may include the features described in eye-mountable device 110, described above in relation to FIG. 1. Other embodiments are possible as well.

V. CONCLUSION

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A method comprising:
   forming a first polymer layer in a molding cavity defined by a first molding piece and a second molding piece, wherein the first polymer layer defines a first side of an eye-mountable device, and wherein the first polymer layer includes an alignment feature, wherein the alignment feature includes an asymmetric peg;
   providing an adhesive in a pattern on a substrate or on the first polymer layer, wherein the substrate has a first surface and a second surface opposite the first surface, and wherein the substrate has a hole with an asymmetric inner diameter such that the hole receives the alignment feature in only a predetermined rotational orientation;
   and wherein the substrate has an electronic component mounted on the second surface;
   adhering the substrate to the first polymer layer while the first polymer layer is on the first molding piece, wherein the adhering comprises (i) positioning the first surface of the substrate on the first polymer layer in the predetermined rotational orientation such that the substrate is aligned with the alignment feature, (ii) applying a force to one or more of the substrate and the first polymer layer, and (iii) curing the adhesive while applying the force; and forming a second polymer layer over the first polymer layer and the second surface of the substrate while the first polymer layer is on the first molding piece, such that the substrate is at least partially enclosed by the first polymer layer and the second polymer layer.

2. The method of claim 1, wherein providing an adhesive in a pattern comprises spraying the adhesive on the substrate or the first polymer layer.

3. The method of claim 1, wherein the adhesive is a silicone adhesive.

4. The method of claim 1, wherein providing an adhesive in a pattern comprises stamping the adhesive on the substrate or the polymer layer.

5. The method of claim 4, wherein the adhesive is stamped using a polydimethylsiloxane (PDMS) stamp.

6. The method of claim 1, wherein the adhesive has a thickness of less than about 5 micrometers.

7. The method of claim 1, wherein the second polymer layer defines a second side of the eye-mountable device.

8. The method of claim 7, wherein the first polymer layer and the second polymer layer comprise a hydrogel material or a silicone elastomer.

9. The method of claim 7, wherein the substrate is more rigid than the first polymer layer and the second polymer layer.

10. The method of claim 7, wherein the second polymer layer is configured to be removably mounted over a corneal surface, and wherein the first polymer layer is configured to be compatible with eyelid motion when the eye-mountable device is so mounted.

11. The method of claim 1, wherein the eye-mountable device has a thickness that is between about 100 micrometers and about 500 micrometers.

12. The method of claim 1, wherein curing the adhesive comprises curing the adhesive using heat, ultraviolet light, or visible light.

13. The method of claim 1, wherein forming a second polymer layer over the first polymer and the second surface of the substrate while the first polymer layer is on the first molding piece comprises forming the second polymer layer between the first molding piece and a third molding piece.

* * * * *